United States Patent [19]

Kraska

[11] 4,173,641

[45] * Nov. 6, 1979

[54] DI-O-N-ALKYL GLYCEROL DERIVATIVES AS IMMUNE STIMULANTS

[75] Inventor: Allen R. Kraska, East Lyme, Conn.

[73] Assignee: Pfizer Inc., New York, N.Y.

[ * ] Notice: The portion of the term of this patent subsequent to Aug. 28, 1996, has been disclaimed.

[21] Appl. No.: 906,260

[22] Filed: May 15, 1978

[51] Int. Cl.$^2$ ............... A61K 31/445; A61K 31/135; C07D 211/26; C07C 91/22
[52] U.S. Cl. .................. 424/267; 260/348.57; 260/465 F; 260/599; 424/330; 546/215; 546/232
[58] Field of Search .............. 260/293.78, 570.6; 424/267, 330; 546/232

[56] References Cited

U.S. PATENT DOCUMENTS

| | | | |
|---|---|---|---|
| 2,738,351 | 3/1956 | Dickison et al. | 260/293.83 |
| 3,432,602 | 3/1969 | Brohult et al. | 424/307 |
| 3,943,173 | 3/1976 | Colella et al. | 260/570.6 |
| 4,012,528 | 3/1977 | Jen | 260/570.6 |
| 4,069,223 | 1/1978 | Adelstein | 260/293.78 |

FOREIGN PATENT DOCUMENTS 51-42177 11/1976 Japan.

Primary Examiner—John M. Ford
Assistant Examiner—Richard A. Schwartz
Attorney, Agent, or Firm—Connolly and Hutz

[57] ABSTRACT

Novel 1,2- and 1,3-(di-O-n-alkyl)glycerol derivatives and their pharmaceutically acceptable acid addition salts are useful as non-specific stimulants of cell-mediated immunity.

18 Claims, No Drawings

DI-O-N-ALKYL GLYCEROL DERIVATIVES AS IMMUNE STIMULANTS

BACKGROUND OF THE INVENTION

This invention relates to novel 1,2- and 1,3-(di-O-n-alkyl) glycerol derivatives, which are useful as non-specific stimulants of cell-mediated immunity in warm-blooded animals. In particular, these novel compounds and related compounds have been found to be useful in the stimulation of antitumoral activity, especially when used in conjunction with conventional cytoreductive therapy. These compounds are also useful as vaccine adjuvants, i.e., are useful in conjunction with known immunological substances in order to induce or enhance the immunogenic response of the latter.

It is known that biological vaccines such as *Corynebacterium parvum* and BCG, a viable strain of *Mycobacterium bovis*, and the synthetic levamisole have utility as immune stimulants of the reticulo-endothelial system and are capable of increasing the resistance of a warm-blooded animal to tumors. However, the use of these agents has been restricted by hepatic-renal toxicity, granuloma formation, neutropenia and inconsistent therapeutic effects. Accordingly, it has been of continuing interest to develop non-biological, systemically active immune stimulants. It has further been of interest to develop compounds which are useful as vaccine adjuvants, in order to induce or enhance the effects of conventional vaccines. For discussions of the stimulation of cell-mediated immunity and antitumoral activity, see Herberman, Adv. Cancer Res., 19, 207 (1971), Jordan and Merigan, Ann. Rev. Pharmacol., 15, 157 (1975), Levy and Wheelock, Adv. Cancer Res., 20, 131 (1972) and Sinkovics, Post Graduate Medicine, 59, 110 (1976).

U.S. Pat. No. 2,738,351 discloses the compounds of the general formula

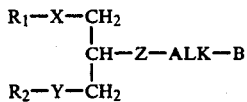

wherein each of $R_1$ and $R_2$ may be alkyl, unsubstituted or substituted aryl or aralkyl, each of X, Y and Z may be oxygen, sulfur or sulfonyl, ALK is straight or branched alkylene of from 1 to 6 carbon atoms, and B may be di(lower)-alkylamino, piperidino, morpholino, pyrrolidino, lower alkyl-pyrrolidino, N'-alkylpiperazino or pipecolino, as local anesthetic agents. Additionally, the discussion of alternate synthetic routes in said patent discloses intermediates of the above formula wherein B is amino and lower alkyl amino. However, none of the compounds specifically enumerated in the disclosure of said patent contains an alkyl $R_1$ or $R_2$ larger than n-pentyl. Further, in none of these compounds are both $R_1$ and $R_2$ alkyl and both X and Y oxygen.

Insecticidal and miticidal compounds of the formula

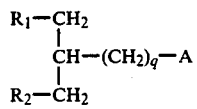

wherein $R_1$ and $R_2$ may each be, inter alia, lower alkylthio; q is 0 to 5 and A may be, inter alia, 1-piperidino or di-lower alkyl amino are disclosed in Japanese Pat. No. J7-6042-177.

Applicant's copending U.S. patent application Ser. No. 825,535 filed Aug. 18, 1977 discloses, inter alia, compounds of the formulae

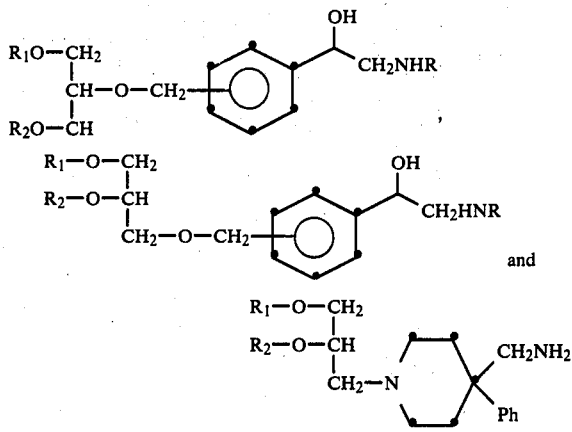

wherein R is hydrogen or alkyl of 1 to 6 carbon atoms and $R_1$ and $R_2$ are each n-alkyl of 12 to 20 carbon atoms. These compounds are disclosed to be useful as antiviral agents.

SUMMARY OF THE INVENTION

The present invention relates to novel compounds selected from those of the formulae

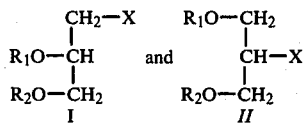

wherein $R_1$ and $R_2$ are each n-alkyl of 8 to 11 carbon atoms; and X is selected from

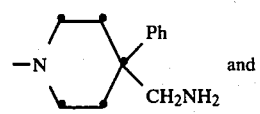

and

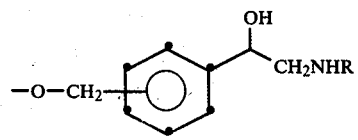

wherein R is hydrogen or alkyl of 1 to 6 carbon atoms, and the pharmaceutically acceptable acid addition salts thereof.

One group of compounds of interest is that where X is 4-aminomethyl-4-phenyl-piperidino. Of these, preferred compounds are those compounds wherein $R_1$ and $R_2$ have the same number of carbon atoms, particularly those where $R_1$ and $R_2$ are each n-decyl. Most preferred of this group are compounds of formula I.

Also of interest are those compounds wherein X is (1-hydroxy-2-alkylaminoethyl)-benzyloxy. Especially preferred are those compounds wherein $R_1$ and $R_2$ have the same number of carbon atoms, particularly those where $R_1$ and $R_2$ are n-decyl. The group R is preferably lower n-alkyl of 1 to 3 carbon atoms, especially ethyl. Compounds of formula I are most preferred.

The present invention also embraces pharmaceutical compositions comprising an immune-stimulant effective amount of a compound of formulae I and II above together with a pharmaceutically acceptable carrier.

Still another feature of the present invention is a method of stimulating non-specific cell-mediated immunity in a warm-blooded animal which comprises administering to said animal an immune-stimulant effective amount of a compound selected from those of the formulae

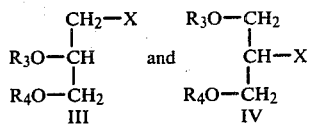

wherein $R_3$ and $R_4$ are each n-alkyl of 8 to 20 carbon atoms; and X is selected from

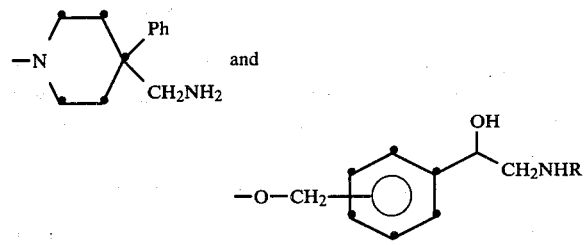

wherein R is hydrogen or alkyl of 1 to 6 carbon atoms, and the pharmaceutically acceptable acid addition salts thereof. Especially preferred is a method where the group X in the compound administered is 4-aminomethyl-4-phenyl-piperidino, especially those wherein $R_1$ and $R_2$ are each of the same number of carbon atoms, particularly n-decyl, and most preferably where the compounds are of formula III.

DETAILED DESCRIPTION OF THE INVENTION

The novel compounds of this invention are derivatives of 1,2-(di-O-n-alkyl)glycerols or 1,3-(di-O-n-alkyl)glycerols and are readily prepared from such compounds by methods familiar to those skilled in the art. The 1,2-(di-O-n-alkyl)glycerol starting materials may be prepared as described by Kates, et al., Biochemistry, 2, 394 (1963). The 1,3-(di-O-n-alkyl)glycerol starting materials may be prepared by the method of Damico, et al., J. Lipid Res., 8, 63 (1967).

Compounds of the present invention wherein the group X is 4-aminomethyl-4-phenyl-piperidino may be prepared from such 1,2- and 1,3-(di-O-n-alkyl)glycerols, for example, by first forming the tosyl derivative of the starting material by reaction with p-toluenesulfonyl chloride and pyridine in a reaction inert solvent, such as methylene chloride, at a temperature of about −10° C. to 40° C., preferably about 10° to 25° C. The tosyl derivative is then reacted with 4-cyano-4-phenyl-piperidine by heating the reactants together at about 75° C. to 250° C. This is preferably done without addition of a solvent, but if desired, a reaction inert solvent such as dimethyl formamide may be employed. The resulting nitrile is then reduced to the desired amine, for example, using Raney nickel and hydrogen.

The compounds of the present invention wherein the group X is (1-hydroxy-2-alkylaminoethyl)-benzyloxy may be prepared by reacting the 1,2- or 1,3-(di-O-n-alkyl)glycerol starting material to form a cyanobenzyl derivative. This may be effected by reaction with an appropriate cyanobenzyl halide, such as cyanobenzyl bromide, in the presence of an alkali metal hydride, for example sodium hydride, in a reaction inert solvent, generally an ether such as tetrahydrofuran, under a nitrogen atmosphere and at a temperature between about 20° C. and 65° C. The cyanobenzyl derivative is reduced to the corresponding formyl benzyl derivative with an alkyl aluminum hydride, such as diisobutyl aluminum hydride, in benzene under nitrogen at about 15°–35° C. The resulting formyl benzyl derivative is then converted to the 1,2-epoxyethyl benzyl derivative by reaction with an alkyl metal hydride suspended in dimethyl sulfoxide in the presence of trimethyl sulfonium iodide, at a temperature of about −5° to 10° C. When the group R is alkyl, the desired product is formed by reaction of the 1,2-epoxyethyl benzyl derivative with an amine $RNH_2$ at a temperature of about 75° C. to 135° C. When R is hydrogen the epoxide is opened by reaction with sodium azide in dioxane at reflux temperature, followed by reduction to the desired amine by contacting with a reducing agent such as lithium aluminum hydride or sodium aluminum hydride in ether at a temperature of about 20° C. to 35° C.

Pharmaceutically acceptable acid addition salts of the amines formed as described above may be prepared by conventional means, such as mixing the appropriate amine and acid in an inert solvent and recovering the salt by evaporation of the solvent or by precipitation of the salt. Hydrochloride salts are readily prepared by passing hydrogen chloride gas through a solution of the amine in an inert solvent. The hydrochloride or dihydrochloride salts obtained by this means tend to contain some water of crystallization, or occluded water. This is not detrimental to the present invention and such compounds may be formulated and administered without further dehydration. It is intended that the claims and specification hereof include both the hydrated and unhydrated compounds. Suitable pharmaceutically acceptable acid salts include such water-soluble and water-insoluble salts as the hydrochloride, hydrobromide, phosphate, nitrate, sulfate, acetate, hexafluorophosphate, citrate, gluconate, benzoate, propionate, butyrate, sulfosalicylate, maleate, laurate, malate, fumerate, succinate, oxalate, tartrate, amsonate (4-4′-diamino-stylbine-2,2′-disulfonate), pamoate (1,1′-methylene-bis-2-hydroxy-3-naphthoate), stearate, 3-hydroxy-2-naphthoate, p-toluenesulfonate, methanesulfonate, lactate and suramin salts.

The compounds represented by formulae III and IV, i.e., the novel compounds of the present invention of formulae I and II and the higher alkyl ether homologs disclosed in applicant's co-pending U.S. patent application Ser. No. 825,535 filed Aug. 8, 1977 have been found to be useful as agents for the non-specific stimulation of cell-mediated immunity in warm blooded animals and, in particular, are useful in the stimulation of the reticulo-endothelial system. The compounds described above can be administered to a warm-blooded animal by a variety of conventional routes, especially intravenously or intraperitoneally, dosages of about 0.5 to 5 mg/kg body weight of the subject to be treated being suitable when administration is by these methods. However, the physician will determine the particular dosage most suitable for the individual patient, which will be dependent on the subject being treated and the particular compound employed. Generally, small doses will be administered initially and may be increased gradually to determine the optimum dosage for the particular subject. The immune competence of the subject will generally be monitored following administration, using conventional techniques employed in the art, such as the monocyte activation and macrophage activation assays described hereinafter. Typically, maximum activation will be observed about 24 to 48 hours after the initial administration and, absent administration of further doses, will decline to the initial level over a further 24 to 48 hour period. Thus, administration of a second dose approximately 24 to 72 hours after the initial administration will maintain the desired level of immune competence. Generally, 2 to 4 doses will be administered in this manner and the response to treatment of the subject determined. Further doses may then be administered if necessary, as described above.

The compounds may be used in pharmaceutical preparations containing the compound or a pharmaceutically acceptable salt thereof in combination with a pharmaceutically acceptable carrier or diluent. A particularly preferred type of pharmaceutical carrier for this purpose is a sterile fat or lipid emulsion vehicle. The latter type of vehicle has been found to be particularly efficacious for parenteral and intravenous administration increasing the therapeutic index to a value of about 15 to 25, whereas with Tween 80-glycerol-water formulations therapeutic indices of about 3 are observed in preliminary tests with mice and rats with the lower alkyl ethers of this invention, for example 4-aminomethyl-1-[2,3-di-n-octyloxy)-n-propyl]-4-phenylpiperidine. Such advantages have been reported for other compounds used with such fat emulsion vehicles, see for example Fortner, et al., American Journal of Hospital Pharmacy, 32, 502 (1975) and Jeppsson, et al., First International Conference on Pharmaceutical technology, Faculty of Pharmacy, Paris-Sud, June 1977. An example of a particularly suitable vehicle is Intralipid (Cutter Laboratories, Berkeley, California), a 10% fat emulsion, based on soybean oil. However, other similar vehicles would be suitable and may be readily prepared by those skilled in the art.

Compounds of formulae III and IV are also useful as vaccine adjuvants and may be used for the purposes and administered by the same methods as presently known adjuvants, see for example, "Immunological Adjuvants", World Health Organization Technical Report Series, No. 595. For example, the compounds of the present invention are useful as adjuvants when used in conjunction with vaccines such as, but not limited to, those for influenza, foot and mouth disease and diphtheria. The compound may be incorporated in the dose of vaccine in an amount of about 1 to 20 mg per dose of vaccine, preferably in a pharmaceutically acceptable carrier, such as a fat or lipid emulsion or glycerol. The vaccine-adjuvant dose is then administered to the subject in the manner conventional for the particular vaccine, generally as a single dose administered subcutaneously or intramuscularly. Alternatively, the adjuvant may be administered independently of the vaccine and either contemporaneously or, preferably, about 8 to 24 hours prior to administration of the vaccine.

The immune stimulant and antitumoral activity of the compounds disclosed herein may be determined by pharmacological tests. Suitable tests include those for the assessment of peritoneal macrophage activation, assessment of tumor rejection (sarcoma 180J model), assessment of delayed cutaneous hypersensitivity and assessment of peripheral monocyte activation. Such tests are more fully described and exemplified hereinafter, together with results obtained therein for compounds of the present invention. Further described are appropriate tests for the evaluation of vaccine adjuvant activity.

The present invention is illustrated by the following examples. It should be understood, however, that the invention is not limited to the specific details of these examples. All temperatures are in degrees centigrade.

EXAMPLE 1

4-Cyano-1-[2,3-(di-n-decyloxy)-n-propyl]-4-phenylpiperidine:

1,2-Di-O-n-propyl)-3-O-(p-tosyl)-glycerol (20 g, 0.0189 mole), prepared from 1,2-di-O-(n-decyl)-glycerol and p-toluenesulfonyl chloride, and 4-cyano-4-phenylpiperidine (4.5 g, 0.024 mole) were combined and heated at 180° C. for 20 minutes. Water (50 ml) and ether (100 ml) were added to the cooled product. The ether layer was isolated and washed with saturated sodium bicarbonate solution (2×100 ml), 1 N hydrochloric acid (100 ml), water (2×100 ml), saturated sodium bicarbonate (100 ml) and water (100 ml). The ether solution was then dried over magnesium sulfate, treated with charcoal, filtered and concentrated to an oil (10 g). The oil was absorbed on silica gel, which was then washed with hexane (3×200 ml), toluene (3×200 ml), chloroform (3×200 ml), and ethyl acetate (3×200 ml). The ethyl acetate was concentrated to give the pure cyano compound: oil, ir (neat) 2220 cm$^{-1}$.

EXAMPLE 2

4-Aminomethyl-1-[2,3-(di-n-decyloxy)-n-propyl]-4-phenylpiperidine:

The nitrile formed in Example 1 (1.2 g, 0.0022 mole) was dissolved in ethanol (50 ml), and the solution was then saturated with ammonia gas. A hydrogenation of this was then carried out at a pressure of 50 p.s.i. for 3 hours using Raney Nickel as catalyst (0.7 g). When the reduction was complete, the mixture was filtered, and the filtrate was concentrated under reduced pressure to an oil (1.1 g). This was chromatographed on silica gel eluted with benzene:ethanol, converted to the hydrochloride salt, and recrystallized from ethyl acetate to give pure hydrochloride (0.32 g, 24% yield): mp 138°–140° C.

Analytical: Calcd for $C_{35}H_{64}N_2O_2.2HCl.\frac{1}{2}H_2O$: C, 66.59; H, 10.78; N, 4.44. Found: C, 66.46; H, 10.56; N, 4.43.

EXAMPLE 3

4-Cyano-1-[2,3-(di-n-hexadecyloxy)-n-propyl]-4-phenylpiperidine:

1,2-Di-O-(n-hexadecyl)-3-O-(p-tosyl)-glycerol was prepared by reacting 1,2-di-O-(n-hexadecyl)-glycerol with p-toluenesulfonyl chloride. Purification was accomplished by recrystallization from ethyl acetate (m.p. 53°–55° C., ir (CHCl$_3$) 1360 and 1180 cm$^{-1}$).

A mixture of 1,2-di-O-(n-hexadecyl)-3-O-(p-tosyl)-glycerol (6.96 g, 10 mmoles), 4-cyano-4-phenylpiperidine hydrochloride (2.23 g, 10 mmoles), triethylamine (2 ml) and N,N-dimethylformamide (40 ml) was stirred for 16 hours at 95° to 100° C. The reaction mixture was then cooled, diluted with water (200 ml) and extracted with ethyl acetate (3×150 ml). The combined ethyl acetate extract was dried over magnesium sulfate, filtered and evaporated in vacuo to an oil (6 g), which was purified by column chromatography (elution with benzene-ethyl acetate) [oil, ir (CHCl$_3$) 2220 cm$^{-1}$].

EXAMPLE 4

4-Aminomethyl-1-[2,3-(di-n-hexadecyloxy)-n-propyl]-4-phenylpiperidine Dihydrochloride A solution of 4-cyano-1-[2,3-(di-n-hexadecyloxy)-n-propyl]-4-phenylpiperidine (2.5 g, 3.6 mmoles) in ether (100 ml) was treated with lithium aluminum hydride (0.4 g, 10.5 mmoles), and the resulting mixture stirred for 4 hours at room temperature. The reaction mixture was treated cautiously with water (100 ml) and extracted with ether (3×100 ml). The combined ether extract was dried over magnesium sulfate, filtered and evaporated in vacuo to an oil, which was purified by silica gel chromatography (elution with benzene:ethanol) and then dissolved in chloroform. The solution was treated with hydrogen chloride gas and then evaporated in vacuo to yield a solid, which was recrystallized from ethyl acetate (1.1 g,), solid contained about ½ mole H$_2$O per mole named product, 40% yield, m.p. 132°–134° C., Elemental analysis calculated: 70.60% C; 11.53% H; 3.50% N. Found: 70.74% C; 11.34% H; 3.40% N.

EXAMPLE 5

Following the procedures of Example 1 through 4, the following compounds were prepared:

EXAMPLE 6

1,2-Di-O-(n-hexadecyl)-3-O-(3-cyanobenzyl)-glycerol

Sodium hydride (50% mineral oil dispersion; 1.056 g, 0.022 mole) was added to a solution of 1,2-di-O-n-hexadecyl glycerol in tetrahydrofuran (150 ml) and stirred for 20 minutes under nitrogen. m-Cyanobenzylbromide (4.0 g, 0.020 mole) was added to the mixture and allowed to react to room temperature overnight. Water (200 ml) and then cautiously added and the aqueous mixture extracted with ethyl acetate (3×150 ml). The extracts were dried over magnesium sulfate, filtered and concentrated under reduced pressure to give an oil (12 g), which was chromatographed on silica gel (eluted with benzene/hexane, 8/2) resulting in pure 1,2-Di-O-(n-hexadecyl)-3-O-(3-cyanobenzyl)-glycerol (8.0 g): oil; ir(CHCl$_3$) 2230 cm$^{-1}$.

EXAMPLE 7

1,2-Di-O-(n-hexadecyl)-3-O-(3-formylbenzyl)-glycerol 1,2-Di-O-(n-hexadecyl)-3-O-(3-cyanobenzyl)-glycerol (5.0 g, 7.6 mmol) was reacted with diisobutylaluminum hydride (1.17 g, 8.2 mmol) in benzene (25 ml) under a nitrogen atmosphere for 16 hours, at ambient temperature. The reaction mixture was treated with methanol (4.22 ml) and water (2.5 ml) and allowed to stir for 30 minutes until any unreacted hydride was decomposed. The mixture was filtered, extracted with benzene (3×25 ml), and the combined benzene extracts were dried with sodium sulfate, filtered and concentrated under reduced pressure. The resulting oil was purified by silica gel chromatography, eluted with benzene, to give pure 1,2-di-O-(n-hexade-

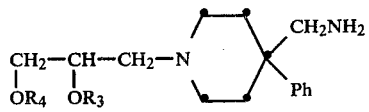

| R$_3$,R$_4$ | mp°C. | Molecular Formula | Calcd % | | Found % | |
|---|---|---|---|---|---|---|
| C$_{16}$H$_{33}$ | 40–42 | C$_{47}$H$_{88}$O$_2$N$_2$ . HCl . H$_2$O | C | 73.53 | C | 73.77 |
| | | | H | 11.94 | H | 11.77 |
| | | | N | 3.64 | N | 3.85 |
| C$_{18}$H$_{37}$ | 115–117 | C$_{51}$H$_{96}$O$_2$N$_2$ . 2HCl | C | 71.95 | C | 71.67 |
| | | | H | 11.60 | H | 11.19 |
| | | | N | 3.29 | N | 3.38 |
| C$_{14}$H$_{29}$ | 140–142 | C$_{43}$H$_{80}$O$_2$N$_2$ . 2HCl | C | 69.46 | C | 69.45 |
| | | | H | 11.25 | H | 11.00 |
| | | | N | 3.75 | N | 3.45 |
| C$_8$H$_{17}$ | 176–178(d) | C$_{31}$H$_{56}$O$_2$N$_2$ . 2HCl . ½ H$_2$O | C | 65.24 | C | 65.27 |
| | | | H | 10.42 | H | 9.90 |
| | | | N | 4.90 | N | 4.95 |

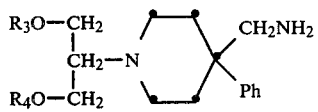

| R$_3$,R$_4$ | mp°C. | Molecular Formula | Calcd, % | | Found, % | |
|---|---|---|---|---|---|---|
| C$_{10}$H$_{21}$ | 190–192 | C$_{35}$H$_{64}$N$_2$O$_2$ . 2HCl . ½ H$_2$O | C | 66.58 | C | 66.70 |
| | | | H | 10.78 | H | 10.20 |
| | | | N | 4.43 | N | 4.27 |

In a similar way further compounds of this invention may be prepared from the appropriate 1,2- or 1,3-(di-n-O-alkyl)glycerol, via the tosyl derivative.

cyl-3-O-(3-formyl benzyl)glycerol 40% yield): oil; ir (CHCl$_3$) 1700 cm$^{-1}$; NMR (CDCl$_3$) δ 10.1 (s, 1, Ar-CHO).

EXAMPLE 8

1,2-Di-O-(n-hexadecyl)-3-O-[3-(1,2-epoxyethyl)-benzyl]-glycerol

Sodium hydride (3.23 g of a 57% dispersion in mineral oil, 0.067 moles) was suspended in dimethylsulfoxide (117 ml) and heated at 70°-75° C. under a nitrogen atmosphere for about 45 minutes, until hydrogen evolution stopped. Tetrahydrofuran (88 ml) was added, and the mixture was cooled to 0°-5° C. Trimethylsulfonium iodide (13.67 g, 0.067 mol) was added in portions, followed by the rapid addition of 1,2-di-O-(n-hexadecyl)-3-O-(3-formylbenzyl)-glycerol (7.0 g, 0.0106 mol) in tetrahydrofuran (58 ml). The mixture was then stirred at room temperature for 16 hours, poured into water (200 ml), and extracted with ether (3×180 ml). The combined ether extracts were washed with water (2×100 ml) and saturated sodium chloride solution (100 ml), dried over magnesium sulfate, filtered and concentrated under reduced pressure to a pale yellow oil (7.0 g, 98% yield), which was pure enough by thin layer chromatography for further reaction, as described in Example 9.

EXAMPLE 9

1,2-Di-O-(n-hexadecyl)-3-O-[3-(1-hydroxy-2-t-butylaminoethyl)benzyl]-glycerol hydrochloride:

t-Butylamine (30 ml) and 1,2-di-O-(n-hexadecyl)-3-O-[3-(1,2-epoxyethyl)-benzyl]-glycerol (2.0 g, 2.97 mmol) were placed in a steel bomb and heated to 100° C. for 9 hours. After cooling the reaction mixture, t-butylamine was removed under reduced pressure and the resulting oil purified by silica gel chromatography, eluted with benzene/ethanol. The desired fractions were saturated with gaseous hydrochloric acid, concentrated under reduced pressure, and recrystallized from ethyl acetate to give pure 1,2-di-O-(n-hexadecyl)-3-O-[3-(1-hydroxy-2-t-butylaminoethyl)-benzyl]-glycerol (630 mg, 27%): mp 49°-51° C.; NMR (CDCl$_3$) δ 1.47 [s, 9, —C(CH$_3$)$_3$].

EXAMPLE 10

1,3-Di-O-(n-decyl)-2-O-[3-(1-hydroxy-2-ethylaminoethyl)benzyl]glycerol hydrochloride Ethylamine (30 ml) and 1,3-di-O-(n-decyl)-2-O-[3-(1,2-epoxyethyl)-benzyl]glycerol (2.018 g; 4.13 mmol) were placed in a steel bomb and heated to 80°-90° C. for 16 hours at 140 p.s.i. After cooling the reaction mixture was washed from the bomb with ether, and the product was isolated by removing the solvent and excess ethylamine under reduced pressure. The resulting oil (2.4 g) was then dissolved in ether, washed with 2% aqueous ammonium hydroxide, water, and saturated aqueous sodium chloride, dried, and concentrated to a yellow oil (1.8 g). The product was purified by silica gel chromatography (eluted with toluene/ethanol: 12/1) and converted to the hydrochloride salt (0.794 g, 33%): mp 55°-57° C.; NMR (CDCl$_3$) δ 0.87 (S, 6H, —C$\underline{H}_3$), 1.3 (S, 32H, aliphatic protons), 1.45 (t, J=7 Hz, 3H, —NHCH$_2$C$\underline{H}_3$), 3.15 (q, J=7 Hz, 2H, —NHC$\underline{H}_2$CH$_3$), 3.45-3.58 [m, 11H, (—C$\underline{H}_2$OCH$_2$)$_2$C$\underline{H}$OR, CHOHC$\underline{H}_2$NH—], 4.65 (S, 2H, Ar—CH$_2$O—), 5.17-5.50 (m, 1H, Ar—C$\underline{H}$OH—), and 7.33 (S, 4H, Ar—$\underline{H}$).

EXAMPLE 11

Following the methods of Examples 6 through 10, the following compounds were prepared.

| R | —OC$_{16}$H$_{33}$ Position | mp°C. | Molecular Formula | Calcd | | Found | |
|---|---|---|---|---|---|---|---|
| CH(CH$_3$)$_2$ | 2,3 | 53-55 | C$_{47}$H$_{89}$O$_4$N . HCl . ½H$_2$O | C | 72.17 | C | 72.11 |
| | | | | H | 11.79 | H | 11.55 |
| | | | | N | 1.79 | N | 1.92 |
| C(CH$_3$)$_3$ | 1,3 | 43-45 | C$_{48}$H$_{91}$O$_4$N . HCl . H$_2$O | C | 71.99 | C | 72.06 |
| | | | | H | 11.83 | H | 11.43 |
| | | | | N | 1.75 | N | 1.71 |

| R | mp°C. | Molecular Formula | Calcd % | | Found % | |
|---|---|---|---|---|---|---|
| CH(CH$_3$)$_2$ | oil | C$_{39}$H$_{73}$O$_4$N . HCl . ½H$_2$O | C | 70.39 | C | 70.36 |
| | | | H | 10.21 | H | 10.77 |
| | | | N | 2.10 | N | 2.22 |
| CH$_2$CH$_3$ | 64-65 | C$_{38}$H$_{71}$O$_4$N . HCl | C | 71.04 | C | 71.04 |
| | | | H | 11.14 | H | 10.99 |
| | | | N | 2.18 | N | 2.08 |

In a similar way further compounds of the present invention may be prepared from the appropriate epoxide and amine.

EXAMPLE 12

Sarcoma 180J Model for Assessment of Tumor Rejection:

Six female CD-1 mice (20-25 g) per group received 10$^6$ S-180J cells which were 5 to 8 days old by intraperitoneal administration. On the day following tumor innoculation the mice received 0.1 ml of the test compound formulated in the fat emulsion vehicle Intralipid (Cutter Laboratories) at the desired dose and were then observed until death or 40 days, whichever occurs first. Results are expressed as increased percent life span (%ILS), defined as follows:

$$\% \, ILS = \frac{\text{Mean Survival of Drug Treated Mice}}{\text{Mean Survival of Untreated Control Mice}} \times 100$$

Results obtained by the above test procedure were as follows:

Table 1

R$_3$—O—CH$_2$
R$_4$—O—CH     CH$_2$NH$_2$
        CH$_2$—N
                Ph

| R$_3$,R$_4$ | %ILS Dose (mg/kg) | | | |
|---|---|---|---|---|
| | 0.25 | 1 | 4 | 16 |
| n-C$_8$H$_{17}$ | 113 | 109 | 154(1) | 192(4) |
| n-C$_{10}$H$_{21}$ | 127 | 139(1) | 110 | 108 |
| n-C$_{14}$H$_{29}$ | 129(1) | 116 | 133 | 109 |
| n-C$_{16}$H$_{33}$ | 110 | 105 | 104 | 127 |
| n-C$_{18}$H$_{37}$ | 119 | 158(2) | 98 | 109 |

Results of the above test obtained with (1-hydroxy-2-alkylamino ethyl)-benzyloxy analogs of this invention formulated in Tween 80-glycerol-water are shown in Table 2.

Table 2

C$_{16}$H$_{33}$O—CH$_2$
           |
           CH —O—⟨benzene ring with OH and NHR substituents⟩
           |
C$_{16}$H$_{33}$O—CH$_2$

| R | —OC$_{16}$H$_{33}$ Position | %ILS Dose (mg/kg) | | |
|---|---|---|---|---|
| | | 5 | 15 | 50 |
| CH(CH$_3$)$_2$ | 2,3 | 174(1) | 135 | 147(1) |
| C(CH$_3$)$_3$ | 2,3 | 166(2) | 181(4) | 182(4) |
| C(CH$_3$)$_3$ | 1,3 | 159(1) | 171(3) | 157(2) |

(Numbers in parentheses in Tables 1 and 2 above are the number of 40 day survivors).

EXAMPLE 13

Assessment of Peritoneal Macrophage Activation

Mice were injected intraperitoneally with saline or the test compound. Macrophages were harvested 72 hours later by intraperitoneal injection of 3 ml 8% fetal calf serum— 92% RPMI 1640 medium (Grand Island Biological Co., N.Y.) (1640$_{92}$ FCS$_8$) plus 5 units/ml of heparin, the temperature of all media being kept at 37° C., lavaged 1 to 2 minutes, opened and all peritoneal fluid drawn off with a sterile, siliconized pipet into a 50 ml plastic tube kept in ice. The macrophages were counted using a hemocytometer and adjusted to a concentration of 1.5×10$^6$/ml with 1640$_{92}$ FCS$_8$. The cells were then placed in multiwell plates, 1.5×10$^6$ cells per well, and incubated for 1 to 2 hours at 37° C. in a 5% carbon dioxide atmosphere. The supernate was discarded and the cells were washed once with media, the macrophages adhering to the bottom of the wells. L 1210 cells (harvested from ascites of DBA mice approximately 5 days after innoculation) in 1640$_{92}$ FCS$_8$ were then added, 1 ml of 1×10$^5$ cells/ml to each well and incubated at 37° C. for 24 to 30 hours in a 5% carbon dioxide atmosphere. The cells were then pulsed with $^3$H-Tdr (1.0μCi/ml; Amersham/Searles) for 6 hours at 37° C., the supernate drawn off using a cell harvester: Reeve-Angel filter, and washed five times with saline. The filter discs were allowed to dry and placed in scintillation vials with LSC scintillation fluid (5.0 g PPO and 0.2 g POPOP/liter toluene; Yorktown Research). Counting was done for 2 minutes using a Beekman LS-250 β-counter. Results obtained by this procedure were as follows:

Table 3

R$_3$—O—CH$_2$
R$_4$—O—CH     CH$_2$NH$_2$
        CH$_2$—N
                Ph

| R$_3$R$_4$ | Dose(mg/kg) | % Inhibition of DNA Synthesis |
|---|---|---|
| n-C$_{10}$H$_{21}$ | 1.25 | 76 |
| n-C$_{10}$H$_{21}$ | 0.625 | 94 |
| n-C$_{10}$H$_{21}$ | 0.313 | 56 |
| n-C$_{14}$H$_{29}$ | 25 | 90 |

EXAMPLE 14

Assessment of Peripheral Blood Monocyte Activation

Rats were injected intravenously with the test compound, or with saline for control animals. The monocytes were harvested 72 hours later by drawing 2 ml blood into an EDTA tube and diluting with 2 ml saline. This was then carefully layered with 3 ml LSM (Lymphocyte Separation Medium—Bionetics) and centrifuged at 800 r.p.m. for 40 minutes at room temperature. A pipet was used to collect the cloudy central layer containing the monocytes and lymphocytes. These cells were washed twice with Hanks Balanced Salt Solution, resuspended in 1640$_{92}$ FCS$_8$, plated in multiwell dishes and incubated at 37° C. in 5% carbon dioxide for 1.5 hours. The cells were then washed vigorously with media to remove non-adherent cells. The remaining monocytes are re-fed media and L1210 cells are added in an Effector:Target ratio of 15:1. Following the procedure described in Example 13 the cells were pulsed with $^3$H-Tdr and counted with a scintillation counter.

Using this procedure, 1.25 mg/kg of 4-aminomethyl-1-[2,3-di-n-decyloxy)-n-propyl]-4-phenylpiperidine resulted in an 80% inhibition of DNA synthesis.

EXAMPLE 15

Vaccine Adjuvanticity—Hemagglutination Inhibition Test

Influenza virus interacts with red blood cells, causing agglutination. If anti-virus antibodies are present in a serum sample, virus-red cell interactions which lead to agglutination are prevented. Thus, the absence of red blood cell agglutination indicates the presence of anti-virus antibodies and determination of the hemagglutination titer, as described hereinafter, provides a measure of the antibody level.

The test compounds at the desired dosage level are formulated by dissolution in 0.3 ml ethanol, followed by the addition of 0.1 ml Tween 80 and the resulting mixture was added to 4.6 ml Intralipid (Cutter Laboratories). Corresponding vehicles without the test compound are also prepared. Fluogen Influenza Virus (Parke-Davis and Co.) was mixed with each vehicle to obtain 250 CCA of antigen per 0.5 ml injection volume. One group of Hartley Female guinea pigs (Camm Laboratories) are injected intramuscularly with 0.5 ml of the vehicle containing the Fluogen and the test compound. A control group of guinea pigs is injected with the vehicle containing Fluogen but no test compound. Thirty days after primary sensitization the animals were challenged by a further intramuscular injection of the homologous antigen with which they were initially immunized. The animals were bled by intracardiac puncture at several times after primary sensitization. Serum was separated using a CORVAC Integrated Serum Separator Tube (Corning Glass Works) and stored at −20° C. until titrated by the hemagglutination test, as follows.

Test sera, treated with 0.011 M potassium iodate to remove nonspecific serum factors that inhibit agglutination, were dispensed in serial two-fold dilutions in 0.025 ml volumes into microtiter wells (Linbro Scientific Company, New Haven, Conn., type IS-MRC-96) containing 0.025 ml of 0.01 M phosphate-buffered physiological saline, (PBS hereinafter) pH 7.2. The test virus suspension, containing HA-4 units per 0.025 ml of PBS, was added to each well: cell (PBS only) and antigen controls (PBS and virus antigen) were included. After incubating the plates at room temperatures for 30 minutes, 0.05 ml of 0.5% saline washed chicken erythrocytes (Flow Laboratories, Rockville, Md.) was added to each well. Incubation continued until the cell control showed normal settling. Periodate-treated sera from normal guinea pigs were included to assess the level of nonspecific agglutination inhibition remaining in the potassium iodate-treated test sera. The hemagglutination inhibition titer was defined as the highest dilution of serum which completely inhibited hemagglutination, corrected for nonspecific inhibition.

Results obtained in tests of 4-aminomethyl-1-[2,3-(di-n-decyloxy)-n-propyl]-4-phenylpiperidine are shown in Table 4. The higher hemagglutination titer observed after rechallenge in those animals to which the test compound was administered shows the adjuvant activity of the compound.

Table 4

| Antigen Administered | Hemagglutination Titer | | | |
|---|---|---|---|---|
| | Day* 15 | 30** | 44 | 65 |
| Fluogen | 0 | 0 | 40 | 40 |
| | 0 | 0 | 160 | 80 |
| | 0 | 0 | 40 | 10 |
| | 10 | 0 | 80 | 10 |
| | 10 | 0 | 80 | 80 |
| | 10 | 0 | 160 | 160 |
| Fluogen and 4-aminomethyl-1-[2,3-(di-n-decyloxy)-n-propyl]-4-phenylpiperidine (5 mg) | 10 | 10 | 80 | 1280 |
| | 10 | 10 | 640 | 2560 |
| | 10 | 40 | 640 | 1280 |
| | 0 | 10 | 640 | 1280 |
| | 0 | 20 | 640 | 160 |
| | 10 | 10 | 10 | 20 |
| | 0 | 10 | 40 | 10 |
| | 10 | 10 | 10 | 10 |
| | 10 | 0 | 10 | 10 |
| | 0 | 0 | — | — |

*Day after primary sensitization
**Rechallenged 30 days after primary sensitization.

Above results are for those observed each animal in respective groups.

What is claimed is:

1. A compound selected from the group consisting of $$\begin{array}{cc} \text{CH}_2\text{—X} & \text{R}_1\text{O—CH}_2 \\ | & | \\ \text{R}_1\text{O—CH} \quad \text{and} & \text{CH—X} \\ | & | \\ \text{R}_2\text{O—CH}_2 & \text{R}_2\text{O—CH}_2 \\ I & II \end{array}$$

and the pharmaceutically acceptable acid addition salts thereof, wherein $R_1$ and $R_2$ are each n-alkyl of 8 to 11 carbon atoms; and X is selected from —N⟨piperidine with Ph and CH₂NH₂⟩ and —O—CH₂—⟨phenyl⟩—CH(OH)CH₂NHR wherein R is hydrogen or alkyl of 1 to 6 carbon atoms and Ph is phenyl.

2. A compound of claim 1 wherein X is

—N⟨piperidine with Ph and CH₂NH₂⟩

3. A compound of claim 2 wherein $R_1$ and $R_2$ each have the same number of carbon atoms.

4. A compound of claim 3 wherein $R_1$ and $R_2$ are each n-decyl.

5. A compound of claim 2, formula I.

6. A compound of claim 4, formula I.

7. A compound of claim 1 wherein X is

—O—CH₂—⟨phenyl⟩—CH(OH)CH₂NHR

8. A compound of claim 7 wherein $R_1$ and $R_2$ each have the same number of carbon atoms.

9. A compound of claim 8 wherein $R_1$ and $R_2$ are each n-decyl.

10. A compound of claim 7 wherein R is ethyl.

11. A compound of claim 8 wherein R is ethyl.

12. A compound of claim 7, formula I.

13. A compound of claim 9, formula I, wherein R is ethyl.

14. A pharmaceutical composition useful for stimulation of non-specific cell-mediated immunity in a warm-blooded animal which comprises an immune-stimulant effective amount of a compound of claim 1 and a pharmaceutically acceptable carrier.

15. A composition according to claim 14 wherein X is

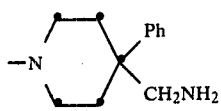

16. A composition according to claim 15, formula I, wherein $R_1$ and $R_2$ are each n-decyl.

17. A method of stimulating non-specific cell-mediated immunity in a warm-blooded animal which comprises administering to said animal an immune-stimulant effective amount of a compound selected from the group consisting of

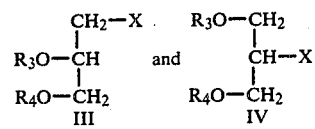

and the pharmaceutically acceptable acid addition salts thereof, wherein $R_3$ and $R_4$ are each n-alkyl of 8 to 20 carbon atoms; and X is selected from

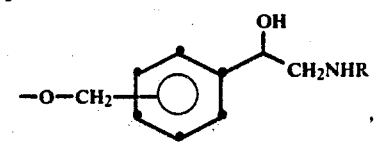

wherein R is hydrogen or alkyl of 1 to 6 carbon atoms and Ph is phenyl.

18. The method of claim 17 wherein X is

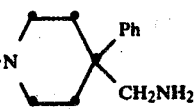

* * * * *